(12) United States Patent
Neyens

(10) Patent No.: US 7,832,294 B2
(45) Date of Patent: Nov. 16, 2010

(54) MEASURING PROBE FOR MEASUREMENTS IN METAL OR SLAG MELTS

(75) Inventor: Guido Jacobus Neyens, Opoeteren (BE)

(73) Assignee: Heraeus Electro-Nite International, N.V., Houthalen (BE)

( * ) Notice: Subject to any disclaimer, the term of this patent is extended or adjusted under 35 U.S.C. 154(b) by 719 days.

(21) Appl. No.: 11/610,571

(22) Filed: Dec. 14, 2006

(65) Prior Publication Data

US 2007/0137324 A1 Jun. 21, 2007

(30) Foreign Application Priority Data

Dec. 15, 2005 (DE) .................. 10 2005 060 492

(51) Int. Cl.
*G01D 21/00* (2006.01)

(52) U.S. Cl. .................................... 73/866.5

(58) Field of Classification Search . 73/864.54–864.59, 73/865.5, 19.01; 266/99; 374/140
See application file for complete search history.

(56) References Cited

U.S. PATENT DOCUMENTS

| 4,401,389 | A | * | 8/1983 | Theuwis ..................... 374/140 |
| 4,451,350 | A | | 5/1984 | Tsuchida et al. |
| 4,830,727 | A | * | 5/1989 | Sasabe et al. ............... 204/412 |
| 4,906,349 | A | | 3/1990 | Beatrice et al. |
| 4,964,736 | A | * | 10/1990 | Cure et al. ................... 374/140 |
| 5,577,841 | A | * | 11/1996 | Wall ........................... 374/140 |
| 5,584,578 | A | * | 12/1996 | Clauss, Jr. .................. 374/140 |
| 5,929,350 | A | * | 7/1999 | Clauss et al. ............... 73/866.5 |
| 6,013,163 | A | * | 1/2000 | Hsia et al. ................... 204/422 |
| 6,200,520 | B1 | | 3/2001 | Morinaka et al. |
| 6,299,348 | B1 | | 10/2001 | Theuwis |
| 6,328,867 | B1 | | 12/2001 | Turkdogan |
| 2005/0184028 | A1 | * | 8/2005 | Baur et al. .................... 216/92 |
| 2006/0236750 | A1 | * | 10/2006 | Gerits ........................ 73/19.01 |

FOREIGN PATENT DOCUMENTS

| DE | 79 25 016 U1 | 2/1980 |
| DE | 30 21 949 C2 | 9/1982 |
| DE | 83 17 634.8 U1 | 6/1984 |
| DE | 35 41 806 C1 | 2/1987 |
| DE | 35 40 228 C2 | 10/1993 |

(Continued)

OTHER PUBLICATIONS

Russian Decision of Grant issued on Apr. 27, 2010 in Russian Application No. 2006144666.

(Continued)

*Primary Examiner*—Robert R Raevis
(74) *Attorney, Agent, or Firm*—Panitch Schwarze Belisario & Nadel LLP

(57) ABSTRACT

A measuring probe is provided for measurements in metal or slag melts, the probe having a measuring head with an immersion end and a rear end, and having sensors arranged on the immersion end with signal lines. The sensors and signal lines are guided through the measuring head by channels, and a separate channel is provided for each sensor. A measuring probe is also provided for measurements in metal or slag melts, the probe having a measuring head with an immersion end and a rear end, having sensors arranged on the immersion end, and having lateral recesses arranged in front of the rear end.

14 Claims, 2 Drawing Sheets

FOREIGN PATENT DOCUMENTS

| | | | |
|---|---|---|---|
| FR | 2 547 656 | * | 6/1984 |
| FR | 2547256 | * | 6/1984 |
| FR | 2 547 656 A1 | | 12/1984 |
| FR | 2547656 A1 | | 12/1984 |
| FR | 2785391 A1 | | 5/2000 |
| GB | 2 312 285 A | | 10/1997 |
| GB | 2312285 A | | 10/1997 |
| JP | 7-151716 | * | 6/1995 |
| JP | 2006250577 A | | 9/2006 |
| SU | 0798591 A1 | | 1/1981 |
| SU | 1249378 A1 | | 8/1986 |
| SU | 1782992 A1 | | 12/1992 |

OTHER PUBLICATIONS

Ukrainian Office Action issued on Jul. 15, 2010 in Ukrainian Application No. a200613186.

* cited by examiner

MEASURING PROBE FOR MEASUREMENTS IN METAL OR SLAG MELTS

BACKGROUND OF THE INVENTION

The invention relates to a measuring probe for measurements in metal or slag melts, having a measuring head, which has an immersion end and a rear end, wherein sensors are arranged on the immersion end.

Such measuring probes are typical in metallurgy and known, for example, from German Patent DE 35 41 806 C1. In this patent, it is disclosed to arrange several sensors and a sample chamber in or on a measuring head. In German Utility Model DE 8317643 U1 a similar measuring probe is disclosed. Here, various sensors and optionally a sample chamber are also arranged in or on a measuring head. The sensors are inserted into the measuring head on the immersion side thereof, and the signal lines are threaded into separate bores and guided rearwardly by these bores through a carrier tube to an evaluation unit. Another measuring probe is known from German Utility Model DE 7925016 U1. Here, several sensors are also arranged on a measuring head and fixed in this measuring head by means of refractory cement.

BRIEF SUMMARY OF THE INVENTION

The invention is based on the problem of improving the known measuring probes, particularly in terms of simple and cost-effective assembly.

A measuring probe with a measuring head, which has an immersion end and a rear end, wherein sensors are arranged on the immersion end, has lateral recesses in front of its rear end according to one embodiment of the invention. In particular, the measuring head can have a lateral, peripheral collar and an end facing away from the immersion end, whose diameter is smaller than the diameter of the collar. A carrier tube can be placed on this end. Connections for sensors can be arranged in the recesses in a simple manner, wherein the recesses are arranged in the measuring head on the side of the collar facing away from the immersion end. The recesses can preferably each be connected to the immersion end of the measuring head by at least one channel. The mounting of the sensors on the immersion end of the measuring head can take place through the channels, whereby the signal lines are guided through the recesses. The recesses and the signal channel leading rearwardly are arranged within a carrier tube. In this way, a very simple mounting of the sensors from only one side of the measuring head is possible.

In another embodiment of the measuring probe according to the invention, the measuring head has an immersion end and a rear end, wherein sensors are arranged on the immersion end with signal lines, which are guided by channels through the measuring head, and wherein a separate channel is provided for each sensor. The measuring probe is characterized in that on the end of a channel facing away from the immersion end, the respective signal lines of the sensor associated with the channel are connected to a contact piece. The contact piece is connected, in turn, to other signal lines, which are guided through a carrier tube of the measuring probe to an evaluation device. The assembly is performed from the rear side of the measuring head, so that rotation of the measuring head during the mounting is not necessary.

In each channel a special sensor is arranged, with individual sensors thereby being arranged with sufficient spacing from each other, so that they have practically no interaction with each other during the measurement and can be individually adapted to special requirements, and so that a universal measuring head can be equipped with different sensors according to necessity and the conditions of the application. During the assembly, for reasons of simplification, all of the measuring heads can first be equipped with sensors to be used in like manner for all applications and then be equipped group-by-group with the respective special sensors for certain applications. Such a modular construction can reduce the assembly costs considerably.

By means of the contact piece the channel can, first of all, be closed and, secondly, the respective sensor can be held in its channel, before the channels are filled together with cement or another refractory material from the immersion side after these channels have been equipped with components, so that the sensors are then fixed. In one such channel a sampling device or an inlet channel of a sampling device arranged on the rear end of the measuring head can also be arranged.

By the arrangement of the so-called contact pieces on the rear end of the measuring head, handling of long signal lines for the assembly of the measuring head is avoided, whereby it is particularly expedient to arrange one respective contact piece in one respective channel and to fix these pieces at the end of the channel facing away from the immersion end. The later assembly of the further-leading signal lines is therefore simpler and error free, because a unique allocation of respective signal cables to the associated contact piece, for example by suitable color markings, nearly rules out any errors.

It is expedient that the end of a channel facing away from the immersion end opens into a recess arranged laterally on the measuring head. In this way, structures projecting from the outer contours of the measuring head are substantially avoided, so that damage during the assembly is prevented. The recesses can be covered with a carrier tube by the assembly of this carrier tube on the measuring head.

Expediently, each channel is formed as a bore and has a greater diameter than the diameter of the associated sensor. The diameters of the bores can also be standardized, so that the flexibility of insertion of the sensors increases. The sensor can be inserted into the channel from the end of the channel facing away from the immersion end until the contact piece, which is connected to the sensor via a relatively short signal cable, touches the channel end. The contact piece can be advantageously set in one channel end. Here, it is particularly advantageous that the contact pieces, at their ends facing away from the immersion end, have a diameter that is greater than the diameter of the respectively associated channel end, because a stop is thereby formed, up to which the contact piece can be inserted into the channel.

The measuring head can have a collar, whose end facing away from the immersion end has a stop for the carrier tube. Typically, such measuring heads have an essentially cylindrical construction or consist of a plurality of cylinders, which are arranged in a line with each other in the axial direction and which have diameters becoming smaller towards the rear (towards the side facing away from the immersion end). In such a case, annular steps are produced. When using such a stepped arrangement, it is expedient that another support tube be arranged on the measuring head inside the carrier tube. This can be advantageous for a sampling device, because in the molten metal, the carrier tube is substantially combusted and loses its stability, so that the support tube arranged therein exerts an additional carrier function for the sample chamber. After removing the measuring probe from the molten metal and after removing the rest of the carrier tube, this inner support tube is removed from the measuring head, so that the sample chamber is easily accessible and can be removed in a simple manner.

Advantageously, a sample chamber and/or expediently also a bath contact is arranged on the measuring head. The bath contact projects from the immersion-side end of the measuring head.

The contacts of the contact piece can sensibly be constructed as plug contacts.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
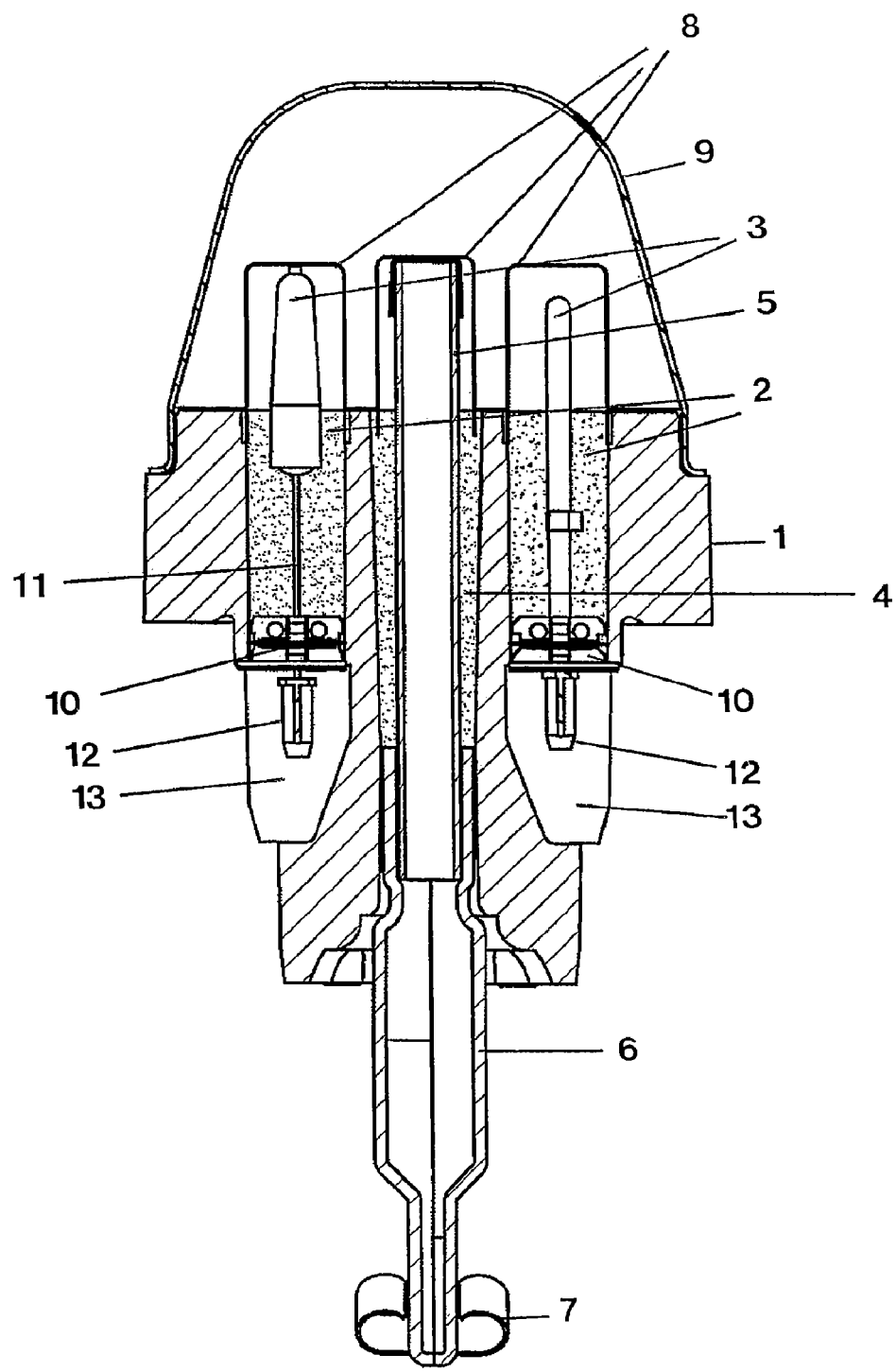
FIG. 1 is a longitudinal section view through a measuring head according to an embodiment of the invention.

In FIG. 1 a measuring head 1 of a measuring probe is shown. The measuring probe is used, for example, in a steel mill for measuring characteristic values of the liquid steel or slag melts. The measuring head has several channels 2. These channels are arranged around a longitudinal axis of the measuring head 1. Sensors 3 (electrochemical sensors, temperature sensors, or other common sensors) are arranged in these channels. A centrally arranged channel 4 carries an inlet tube 5 for a sample chamber 6. The sample chamber 6 is fixed at the end of the measuring head 1 facing away from the immersion end. In FIG. 1 a typical half-shell sampling device is shown, whose rear end is held together with a clamp 7. The channels 2, 4 are filled with refractory cement, so that the inlet tube 5 and the sensors 3 are fixed. The ends of the sensors 3 or the inlet tube 5 projecting beyond the immersion end of the measuring head 1 are covered respectively with separate protective caps 8 adapted to the specific purpose. The protective caps 8 protect the sensors 3 and the inlet tube 5 upon plunging through the slag melt. The entire measuring head 1 is covered on its immersion end with a single additional cap 9, which is stable and protects the protective caps 8 lying underneath it during transport or when pushing through the crusted slag.

The sensors 3 are connected either directly or via signal lines 11 to a respective contact piece 10. In FIG. 1 an oxygen sensor is shown on the left and a thermoelement is shown on the right. The contact pieces 10 close the respective rear ends of the channels 2. On their rear ends, the contact pieces 10 have plug contacts 12, which are arranged in recesses 13 of the rear end of the measuring head 1. The recesses 13 were formed in a manner known per se during the manufacture of the measuring head 1 (just as the channels were) as part of the molded part, but they can also be milled at a later time.

Figure 2:
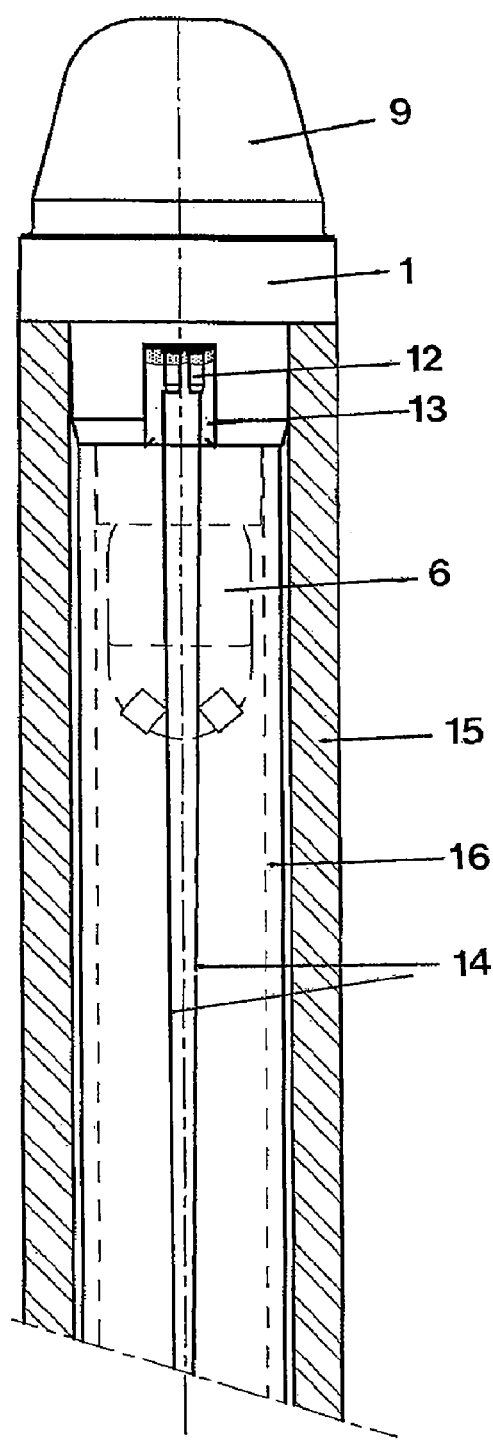
FIG. 2 is a longitudinal schematic view, partially in section, of a measuring probe according to an embodiment of the invention with a carrier tube.

FIG. 2 shows the measuring head 1 covered with an external cap 9. Plug contacts 12 are arranged within a recess 13 on the rear end of the measuring head. The plug contacts 12 are connected to further signal lines 14, which are guided, in turn, through a carrier tube 15 and which are connected to evaluation electronics. On a second, reduced diameter of the rear end of the measuring head 1, a support tube 16 is arranged, which additionally protects the sample chamber 6 and ensures a simple removal of the sample chamber 6 after the sample taking.

The individually mounted sensors 3 have practically no effect on each other and can be adapted to the special purpose of the application. The sampling device is effectively protected from the penetration of slag, because the dimensioning of the protective caps can be set, so that the inlet of the inlet tube 5 is opened for the first time in the molten steel. The assembly of additional elements of the measuring head 1 (sensors 3, sample chamber 6) is performed from one side of the measuring head 1. The pouring of refractory cement is performed from the other side, so that the measuring head 1 can be handled easily during the assembly and does not have to be rotated constantly. All of the connections are easily visible and therefore can be monitored during the production. Long wires, which could cause interference during the assembly of the measuring head 1, are not present and the number of necessary firing operations for firing the refractory cement is minimized.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A measuring probe for making measurements in metal or slag melts, the probe comprising a measuring head having an immersion end, a rear end and channels running through the measuring head from the immersion end to the rear end, sensors arranged on the immersion end with signal lines, the sensors and signal lines being arranged in the channels, wherein a separate channel is provided for each sensor, and contact pieces on ends of the channels facing away from the immersion end, wherein the signal lines of associated sensors are connected to respective contact pieces, and wherein each contact piece is arranged on one respective channel and is fixed on the end of the channel facing away from the immersion end.

2. The measuring probe according to claim 1, wherein the ends of the channels facing away from the immersion end are adjacent at least one recess arranged laterally on the measuring head.

3. The measuring probe according to claim 1, wherein the channels are formed as bores having a greater diameter than a diameter of the associated sensor.

4. The measuring probe according to claim 1, wherein the contact pieces are respectively inserted each into one of the channel ends.

5. The measuring probe according to claim 4, wherein the contact pieces, at their ends facing away from the immersion end, have a diameter greater than a diameter of the respectively associated channel end.

6. The measuring probe according to claim 1, wherein the measuring head is arranged in an opening of a carrier tube.

7. The measuring probe according to claim 6, wherein a support tube is arranged on the measuring head within the carrier tube.

8. The measuring probe according to claim 1, further comprising a bath contact arranged on the measuring head.

9. The measuring probe according to claim 1, further comprising a sample chamber arranged on the measuring head.

10. The measuring probe according to claim 1, wherein contacts of the contact pieces have a form of plug contacts.

11. A measuring probe for making measurements in metal or slag melts, the probe comprising a measuring head having an immersion end, a rear end and channels running through the measuring head from the immersion end to the rear end, sensors arranged on the immersion end with signal lines, the sensors and signal lines being guided by arranged in the channels, contact pieces fixed on ends of the channels facing away from the immersion end, wherein the signal lines are connected to the contact pieces, and at least one recess arranged laterally on the measuring head, wherein the ends of the channels facing away from the immersion end open into the at least one recess.

12. The measuring probe according to claim 11, further comprising a lateral, peripheral collar arranged on the measuring head, and the rear end has a smaller diameter than a diameter of the collar.

13. The measuring probe according to claim 12, wherein the at least one recess is arranged on the measuring head on a side of the collar facing away from the immersion end.

14. The measuring probe according to claim 11, wherein further signal lines are connected to contacts of the contact pieces within the at least one recess for leading rearwardly in signal channels arranged within a carrier tube.

* * * * *